(12) United States Patent
Yoneda et al.

(10) Patent No.: US 6,380,424 B1
(45) Date of Patent: Apr. 30, 2002

(54) PURIFICATION PROCESS FOR HYDROXYALKYL (METH)ACRYLATE

(75) Inventors: Yukihiro Yoneda, Himeji; Fumio Shibusawa, Ibo-gun; Yasuhiro Shingai; Masatoshi Ueoka, both of Himeji, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 4 days.

(21) Appl. No.: 09/664,967

(22) Filed: Sep. 16, 2000

(30) Foreign Application Priority Data

Oct. 7, 1999 (JP) .............................. 11-286974

(51) Int. Cl.⁷ .................... C07C 67/26; C07C 67/48; C07C 69/52
(52) U.S. Cl. ................ 560/209; 560/209; 560/218; 560/205
(58) Field of Search ............... 560/209, 218, 560/205

(56) References Cited

U.S. PATENT DOCUMENTS

| 4,261,798 A | 4/1981 | Palmer |
| 4,365,081 A | 12/1982 | Shimizu et al. |
| 4,369,097 A | 1/1983 | Nezu et al. |
| 5,206,421 A | * 4/1993 | Sato et al. |

FOREIGN PATENT DOCUMENTS

| DE | 152 540 | 12/1981 |
| JP | 57-300 B2 | 1/1982 |
| JP | 60-43056 B2 | 9/1985 |
| JP | 7-10794 B2 | 2/1995 |
| JP | 11-240853 A | 9/1999 |

* cited by examiner

*Primary Examiner*—James O. Wilson
*Assistant Examiner*—Farhad Forohar

(57) ABSTRACT

The present invention provides: a purification process for hydroxyalkyl (meth)acrylate that suppresses forming by-products such as a diester and a dimer of acrylic acid in the distillation process, and can ensure a purity of hydroxyalkyl (meth)acrylate, and can operate stably without causing troubles such as polymerization. In a purification process for hydroxyalkyl (meth)acrylate which is obtained by reacting (meth)acrylic acid and alkylene oxide in the presence of a catalyst, and removing unreacted alkylene oxide and/or (meth)acrylic acid in a reaction solution after the reaction, a distillation apparatus having a portion of a vacant column and a thin-film evaporation apparatus are used at the same time.

5 Claims, 2 Drawing Sheets

PURIFICATION PROCESS FOR HYDROXYALKYL (METH)ACRYLATE

BACKGROUND OF THE INVENTION

A. Technical Field

The present invention relates to a purification process for hydroxyalkyl (meth)acrylate.

B. Background Art

Hydroxyalkyl (meth)acrylate is generally obtained by reacting (meth)acrylic acid and alkylene oxide in the presence of a catalyst. However, hydroxyalkyl (meth)acrylate is formed as an objective product and at the same time by-products such as alkylene glycol di(meth)acrylate (hereinafter donated to "diester"), dialkylene glycol (meth)acrylate and a dimer of acrylic acid are formed in this production process. Accordingly, a purification process is necessary.

As a general purification process up to this day, a process comprising the step of distilling a reaction solution in a reduced pressure in order to separate and purify is carried out (JP-B-300/1982). However, in this process, for example, in case where a distillation column was used, hydroxyalkyl (meth)acrylate coexistent with a catalyst used for the reaction for a long time was exposed to a comparatively high temperature. Therefore, the diester and the dimer of acrylic acid produced from remaining acrylic acid were increased, a purity of hydroxyalkyl (meth)acrylate as an objective product lowered and a problem as to a production quality rose because disproportionation reaction of this hydroxyalkyl (meth)acrylate was apt to occur. In addition, there is another problem that polymerization of hydroxyalkyl (meth)acrylate is apt to occur in staying at a high temperature because hydroxyalkyl (meth)acrylate has a very high polymerizability.

On the other hand, a process utilizing a thin-film evaporation apparatus (which might be called thin-film evaporator) was considered (German Patent No. 152540) in order to avoid long staying at a high temperature. However, this process was excellent in suppression of by-products and inhibition of polymerization, and the thin film of evaporating surface was maintained by rotating a cylindrical object and paddling a solution on the evaporating surface with a wiper in the thin-film evaporation apparatus. However, there were problems that a splash and an entrainment easily produced by rotating and paddling in order to form a liquid film and a distilled product is easily contaminated with the splash and the entrainment.

SUMMARY OF THE INVENTION

A. Object of the Invention

An object of the present invention is to provide: a purification process for hydroxyalkyl (meth)acrylate that suppresses forming by-products such as a diester and a dimer of acrylic acid in the distillation process, and can ensure a purity of hydroxyalkyl (meth)acrylate, and can operate stably without causing troubles such as polymerization.

B. Disclosure of the Invention

The present inventors diligently studied to solve the above-mentioned problems. As a result, they hit on an idea that: in a purification process for hydroxyalkyl (meth)acrylate, which comprises the steps of obtaining a reaction solution by reacting (meth)acrylic acid and alkylene oxide in the presence of a catalyst, removing unreacted alkylene oxide and/or (meth)acrylic acid in the reaction solution, and thus obtaining the hydroxyalkyl (meth)acrylate, a mode that a distillation apparatus having a portion of a vacant column and a thin-film evaporation apparatus are used at the same time is adopted, thereby purification of hydroxyalkyl (meth)acrylate can be carried out without causing prior problems owing to a multiplicated effect derived from characteristics that these apparatuses have respectively and using these apparatuses at the same time. Concretely, they found that: a residence time for a solution at a high temperature can be shortened in the presence of the catalyst by using the thin-film evaporation apparatus at the same time, impurities can be suppressed to form, and a purity of a product can be ensured if the problem of contaminating with the splash and the entrainment is caused not to arise by returning the treated product to the distillation apparatus. The present invention was completed in this way.

That is to say, a purification process for hydroxyalkyl (meth)acrylate, according to the present invention, comprises the steps of: obtaining a reaction solution by reacting (meth)acrylic acid and alkylene oxide in the presence of a catalyst, removing unreacted alkylene oxide and/or (meth)acrylic acid in the reaction solution, and thus obtaining the hydroxyalkyl (meth)acrylate, and this purification process is characterized in that a distillation apparatus having a portion of a vacant column and a thin-film evaporation apparatus are used at the same time.

These and other objects and the advantages of the present invention will be more fully apparent from the following detailed disclosure.

Explanation of the Symbols

Figure 1:
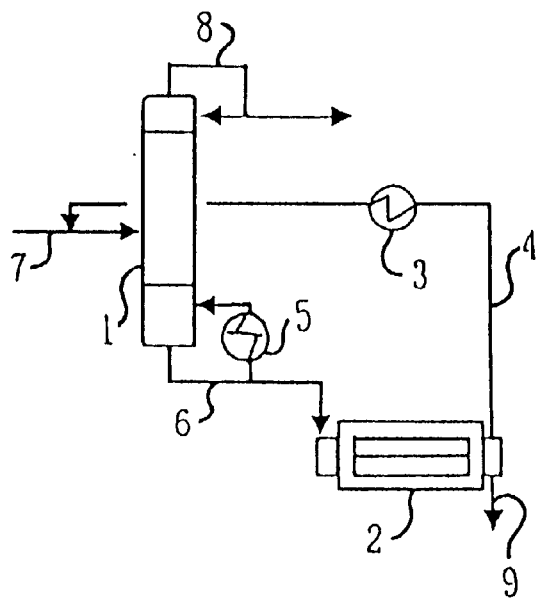
FIG. 1 is a flow chart describing one example of a purification process according to the present invention.

1: Distillation column
2: Thin-film evaporation apparatus
3: Condenser
4: Distillate line
5: Reboiler
6: Extracting line from distillation column bottom
7: Supplying line to distillation column
8: Distillate line for ester
9: Extracting line for waste fluid
12: Thin-film evaporation apparatus
13: Supplying line to thin-film evaporation apparatus
14: Distillate line for ester
15: Extracting line for waste fluid
21: Distillation column
23: Supplying line to distillation column
24: Distillate line for ester
25: Extracting line for waste fluid

DETAILED DESCRIPTION OF THE INVENTION

At a summary of a production process for hydroxyalkyl (meth)acrylate, that can be preferably applied to a characteristic purification process according to the present invention, is explained later. Namely, to begin with, (meth) acrylic acid and alkylene oxide undergo addition reaction in the presence of a catalyst. In this case, reaction molar ratio of alkylene oxide to (meth)acrylic acid is often raised, Even if a conversion of acrylic acid is 100%, unreacted alkylene oxide remains in a reaction solution after the reaction. If the conversion of acrylic acid is less than 100%, unreacted (meth)acrylic acid and alkylene oxide remains in a reaction solution after the reaction generally. Accordingly, the above reaction solution is introduced into a process to remove these unreacted raw materials from the reaction solution. Then, purification such as distillation is performed as a final step and hydroxyalkyl (meth)acrylate as an objective product can be obtained. The present invention relates to a purification process that is the final step for the above production process.

When carrying out the present invention, raw materials preferably used for producing hydroxyalkyl (meth)acrylate that is an object to be purified are (meth)acrylic acid and alkylene oxide. (Meth)acrylic acid used in the present invention means acrylic acid or methacrylic acid. In addition, alkylene oxide used in the present invention is preferably alkylene oxide having 2 to 6 carbons, more preferably, that having 2 to 4 carbons. Examples thereof include ethylene oxide, propylene oxide and butylene oxide.

When carrying out the present invention, as a mixing ratio of raw materials in the reaction of above (meth)acrylic acid and alkylene oxide, the ratio of alkylene oxide is preferably in the range of 1.0 mole or more by 1 mol of (meth)acrylic acid, more preferably in the range of 1.0 to 2.0 mole, still more preferably in the range of 1.03 to 1.7 mol, most preferably in the range of 1.1 to 1.5 mole. In the case where the mixing ratio of alkylene oxide is less than 1.0 mole, it is unpreferable because the reaction ratio becomes lower and by-products increase. In addition, in the case where the mixing ratio of alkylene oxide is too much, it is unpreferable because of economy.

In the present invention, reaction between (meth)acrylic acid and alkylene oxide in the presence of a catalyst can be carried out according to a process that is generally used in this kind of reaction. The reaction is carried out by introducing liquid alkylene oxide into (meth)acrylic acid. On this occasion, alkylene oxide can be added in batch operation, in continuous operation or in intermittent operation. And in case where alkylene oxide is added in continuous operation or in intermittent operation, as is carried out in this kind of reaction, the reaction can be completed by the so-called maturing that is performed by continuing the reaction after introducing alkylene oxide. Reaction temperature thereof is usually preferably in the range of 40 to 130° C., more preferably in the range of 50 to 100° C. In case where the reaction temperature is lower than 40° C., the proceeding of the reaction becomes too late and apart from a practical level. On the other hand, in case where the reaction temperature is higher than 130° C., it is unpreferable because polymerization of (meth)acrylic acid or produced ester and denaturalization of a product arise. Pressure in the reaction system depends upon kinds of raw materials or mixing ratio thereof but the reaction is usually carried out under an increased pressure. In addition, atmosphere of the reaction is not especially limited, but the reaction is carried out under condition of using inert gas such as nitrogen.

When carrying out the present invention, catalysts preferably used for producing hydroxyalkyl (meth)acrylate that is an object to be purified are not especially limited and catalysts generally used in this kind of reaction can be utilized. Example such as: iron compounds such as ferric chloride and ferric acetate; chromium compounds such as sodium dichromate, chromium chloride and chromium salts of an unsaturated acid; amines such as trialkylamines and ion-exchange resin containing a tertiary ammonium group can be utilized.

Stabilizers used in the reaction in order to prevent (meth) acrylate from polymerizing are not especially limited and polymerization inhibitors generally used in this kind of reaction can be utilized. Examples thereof include phenol compounds such as hydroquinone, methylhydroquinone, tert-butylhydroquinone, 2,6-di-tert-butylhydroquinone, 2,5-di-tert-butylhydroquinone, 2,4-dimethyl-6-tert-butylphenol and hydroquinone monomethyl ether; p-phenylenediamines such as N-isopropyl-N'-phenyl-p-phenylenediamine, N-(1, 3-dimethylbutyl)-N'-phenyl-p-phenylenediamine, N-(1-methylheptyl)-N'-phenyl-p -phenylenediamine, N,N'-diphenyl-p-phenylenediamine and N,N'-di-2-naphthyl-p-phenylenediamine; amines such as thiodiphenylamine and phenothiazine; copper dialkyldithiocarbamates such as copper dibutyldithiocarbamate, copper diethyldithiocarbamate and copper dimethyldithiocarbamate; nitroso compounds such as nitrosodiphenylamine, isoamyl nitrite, N-nitrosocyclohexylhydroxylamine, N-nitroso-N-phenyl-N-hydroxylamine and their salts; and N-oxyl compounds such as 2,2,4,4-tetramethylazetidine-1-oxyl, 2,2-dimethyl4,4-dipropylazetidine-1-oxyl, 2,2,5, 5-tetramethylpyrrolidine-1-oxyl, 2,2,5,5-tetramethyl-3-oxopyrrolidine-1-oxyl, 2,2,6,6-tetramethylpiperidine-1-oxyl, 4-hydroxy-2,2,6, 6-tetramethylpiperidine-1-oxyl, 6-aza-7,7-dimethyl-spiro[4, 5]decane-6-oxyl, 2,2,6,6-tetramethyl-4-acetoxypiperidine-1-oxyl and 2,2,6,6-tetramethyl-4-benzoyloxypiperidine-1-oxyl. Representative examples thereof include hydroquinone, hydroquinone monomethyl ether, phenothiazine and copper dibutyldithiocarbamate. The used amount of the polymerization inhibitor is usually in the range of 0.001 to 1 weight % by (meth)acrylic acid and preferably in the range of 0.01 to 0.5 weight %.

The characteristic of the present invention is that: in case where the reaction solution obtained as mentioned above is purified by distillation, a distillation apparatus having a portion of a vacant column and a thin-film evaporation apparatus are used at the same time.

The distillation apparatus having a portion of a vacant column is preferably the so-called distillation column. The structure thereof can be simple distillation and examples thereof include rectifying columns such as a packed column, a bubble cap tower and a perforated-plate column. Especially, the structure is preferably a distillation column comprising plural sieve trays or a distillation column comprising packed materials. In case of the simple distillation, it is preferable that an distillation apparatus comprises wire mesh that is mounted in order to prevent a splash and an entrainment from being accompanied. In addition, a multi-plated perforated-plate column is preferable in view of ensuring purity and removing a polymerized product. In the method of heating, jacket type heaters, or shell-and-tube heat-exchangers with circulated a bottom are included. As to pressure condition of the distillation, the distillation is carried out in a reduced pressure. An operating pressure thereof is preferably as low as possible in view of inhibiting from polymerization, but is preferably in the range of 0.66 to 40 hPa, more preferably in the range of 1.33 to 13 hPa, still more preferably in the range of 4 to 9.3 hPa. A solution temperature in the distillation apparatus is usually in the range of 70 to 130° C., preferably in the range of 80 to 110° C.

It is a preferable mode that the distillation apparatus having a portion of a vacant column comprises a reboiler in the present invention. The thin-film evaporation apparatus used with the distillation apparatus at the same time may play a part as a reboiler when a handling amount is small. However, the area of heat transfer thereof is lacking when the handling amount is large. Therefore, the above problem can be avoided by further using the thin-film evaporation apparatus at the same time. Forms of the reboiler are not especially limited, but examples of shell-and-tube heat exchanger include a longitudinal thermosiphon reboiler, a longitudinal shell-and-tube liquid film downstream reboiler and a forced-circulation boiler. The forced-circulation boiler of which heat transfer surface has hardly any gas phase is preferable in view of inhibiting polymerization. In addition, the longitudinal shell-and-tube liquid film downstream reboiler has a short residence time of a solution because heat transfer surface thereof is usually wet with the solution and holdup of the solution is small, and is preferable because of inhibiting polymerization and formation of impurities.

The thin-film evaporation apparatus utilized in the present invention may include any of a longitudinal one and a horizontal one. Examples of the longitudinal include a distillation apparatus comprising a vertical rotation axis in a cylinder comprising a jacket, that makes a thin film by using a stirring vane or a wiper in order to evaporate, such as Smith thin-film evaporation apparatus and Luwa thin-film evaporation apparatus. Examples of the horizontal include a distillation apparatus comprising a horizontal rotation axis in a cylinder comprising a horizontal jacket, that makes a thin film by rotating a roller or a wiper in order to evaporate.

A pressure condition of the thin-film evaporation apparatus is preferably a condition close to that of the distillation apparatus, more preferably the same condition as that of the distillation. Particularly, when carrying out the present invention, it is preferable that the distillation apparatus having a portion of a vacant column is operated at operating pressure of 0.66 to 40 hPa and the thin-film evaporation apparatus is operated at operating pressure of 0.66 to 40 hPa. Temperature of the thin-film evaporation apparatus can be maintained more lower by controlling the operating pressure in this way. Even in a condition of raising the ratio of the feed amount to the bottom amount (feed amount/bottom amount, hereinafter referred to as concentration ratio), it is preferable because formation such a dimer and by-products can be suppressed, there is no trouble of polymerized products, and a stable operation can be carried out.

As the distillation apparatus having a portion of a vacant column and the thin-film evaporation apparatus are used at the same time in the present invention, the concentration ratio of the distillation apparatus can be lowered, the rise of temperature at the apparatus bottom can be diminished, amount of extract from the distillation apparatus is increased and residence time of a solution at the apparatus bottom can be diminished. Therefore, formation of the diester and high boiling materials in the distillation apparatus can be suppressed. In addition, anxiety about a trouble of polymerization is also a little.

Even if the concentration ratio of the distillation apparatus is low, the concentration ratio of the thin-film evaporation apparatus used at the same time can be raised. The thin-film evaporation apparatus has the advantage that the diester and the high boiling components are formed a little. Splash components and entrainment components contained in a distilled vapor and in a condensate of the thin-film evaporation apparatus are returned to the distillation apparatus and separated as described later. Therefore, the product is not contaminated with the splash and the entrainment from the thin-film evaporation apparatus.

If purification is carried out with the distillation apparatus alone, the ratio of the distillate amount to the feed amount (distillate amount/feed amount, hereinafter referred to as distillate ratio) should be diminished in order to obtain purity. Accordingly, yield is diminished. On the other hand, simple distillation can be carried out, but an distillation efficiency will be raised by placing packed materials or a tray in the distillation apparatus and bringing into gas-liquid contact in order to raise the distillate ratio and improve the yield. However, raising the distillate ratio means raising the concentration ratio. If the concentration ratio arises, the amount of extract from the distillation apparatus bottom becomes decreased and the residence time becomes increased. In addition, if the concentration ratio rises, a high boiling compound is concentrated and solution temperature of the distillation apparatus bottom rises according to the rise of boiling point. The higher the temperature is and the longer the residence time is, the more the diester forms. Therefore, raising the concentration ratio causes raising the temperature and increasing the residence time, and forming diester comes into question. In addition, the higher the temperature is and the longer the residence time is, the more the polymerization occurs. Therefore, a possibility of happening a trouble increases. Furthermore, if a distillation efficiency is improved by comprising a tray (trays) or packed materials in the distillation apparatus, especially in the range of low pressure condition (in high vacuum range), pressure loss of the tray(s) or the packed materials influences the rise of pressure of the column bottom greatly. Especially if the temperature rises according to the rise of pressure, it is unpreferable in view of polymerization and forming the diester.

In addition, if purification is carried out with the thin-film evaporation apparatus alone, it is preferable in view of suppressing the diester and it is possible to raise the concentration ratio because the residence time of the solution decreases. In addition, formation of the diester and the high boiling compound is suppressed because the residence time is short. Even in the same concentration ratio, the rise of the boiling temperature with the thin-film evaporation apparatus is less than that with the distillation apparatus alone and the temperature can be kept low. However, distillation vapor from the thin-film evaporation apparatus is apt to be contaminated by accompanying a splash and an entrainment of a concentrated solution thereof and the product is contaminated with impurities having a high boiling point. Therefore, there is a disadvantage that a highly pure product is not obtained. Furthermore, in the thin-film evaporation apparatus, the thin film of evaporating surface is maintained by rotating a cylindrical object and paddling a solution on the evaporating surface with a wiper. However, a splash and an entrainment are easily produced by rotating and paddling in order to form the liquid film and are easily contaminated into a distilled product. In this way, accompanying the splash and the entrainment are a remarkable disadvantage in the thin-film evaporation apparatus and it is not necessary enough even if prevented by wire mesh.

In addition, in the purification process for hydroxyalkyl (meth)acrylate according to the present invention, it is a preferable mode that a bottom of the distillation apparatus is supplied to the thin-film evaporation apparatus and a distillate from the thin-film evaporation apparatus is returned to the distillation apparatus having a portion of a vacant column through a distillate line comprising a condenser on the way.

It is preferable that the rise of temperature of the distillation apparatus through the distillate line too high can be suppressed and a trouble as to especially highly polymerizable material decreases by placing the condenser on the way of the distillate line from the thin-film evaporation apparatus and supplying the distillate to the distillation apparatus. In addition, it is preferable to place the condenser because the temperature of the thin-film evaporation apparatus can be lowered by being possible to have another vacuum system in addition to that of the distillation apparatus and it is possible to further concentrate. In particular, it is preferable in view of inhibiting polymerization and improving efficiency that the condenser is placed on the way from of the distillate line from the thin-film evaporation apparatus because hydroxyalkyl (meth)acrylate as an object product for purification is especially polymerizable.

If the vapor kept intact from the thin-film evaporation apparatus is supplied to the distillation apparatus without placing the condenser and an object product for purification is not very polymerizable, supplying the vapor to the distillation apparatus is economical in view of energy cost. However, if an object product for purification is highly polymerizable described in the present invention and the vapor kept intact from the thin-film evaporation apparatus is supplied to the distillation apparatus without placing the condenser, problems such as polymerization may occur.

A portion where a solution of the distillate line returns is not especially limited if the portion is a portion where the solution returns to the distillation apparatus having a portion of a vacant column. The solution may return directly to the evaporation apparatus by way of a tank. The solution may return to a supplying pipe arrangement of the evaporation apparatus. In addition, not whole amount but partial amount may return, for example, partial amount may be used for mother liquor in order to prepare a stabilizer. It is a preferable mode that whole amount returns to the supplying pipe arrangement of the evaporation apparatus.

Forms of condensers used in the present invention are not especially limited, but examples thereof include a barometric condenser, a longitudinal shell-and-tube condenser and a horizontal shell-and-tube condenser. The barometric condenser or the longitudinal shell-and-tube condenser is preferable in view of inhibiting polymerization. In the case of tube side condensation of the longitudinal shell-and-tube condenser, it is preferable in view of inhibiting polymerization and operating stably that a distillate is circulated and showers into the vapor like the barometric condenser.

In the purification process for hydroxyalkyl (meth) acrylate according to the present invention, it is preferable that the above distillation is carried out in the presence of oxygen containing gas (0.5 to 100 vol %) in addition to a polymerization inhibitor in order to inhibit polymerization. Oxygen gas or air may be utilized as the oxygen containing gas. The addition amount of the oxygen containing gas is preferably 0.01 vol % or more, and less than 10 vol % by the amount of a top vapor. In case where the addition amount is 10 vol % or more, it is not preferable because it is difficult to condense the vapor with the condenser and loss of the product increases. A place where the oxygen containing gas is added is not especially limited, but it is effective if the oxygen containing gas is added to: heating portions such as an inlet of the reboiler where a process fluid is circulated and an inlet of the thin-film evaporation apparatus; portions where a fluid stays and in a liquid and/or gas phase of the distillation apparatus, such as a fluid in a bottom of the distillation apparatus; or at least one portion selected from the group consisting of the aforementioned portions, the below-mentioned portions, a vapor line and a condenser.

A portion where the polymerization inhibitor is added is not especially limited, but examples thereof include portions such as (meth)acrylic acid as a raw material, alkylene oxide as a raw material, a reactor, a solution after the reaction, a supplied solution in order to purify, a purified distillate and a supplied solution to the thin-film evaporation apparatus. Examples of the polymerization inhibitors are listed as mentioned above.

EFFECTS AND ADVANTAGES OF THE INVETION

The purification process according to the present invention, enables to ensure highly pure hydroxyalkyl (meth)acrylate stably by inhibiting to form by-products such as a diester and polymerized products and ensuring purity of hydroxyalkyl (meth)acrylate by use of a distillation apparatus, because a residence time is short at high temperature.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited to the below-mentioned examples.

Constituent analysis of supplied solutions and distillates in the below-mentioned examples and comparative examples is carried out with gas-chromatography.

EXAMPLE 1

2-Hydroxyethyl methacrylate was purified by using a distillation column and a thin-film evaporation apparatus at the same time according to the process as described in FIG. 1. The distillation column 1 as used was a dam-free perforated-plate distillation column having five plates and the thin-film evaporation apparatus 2 was a horizontal thin-film evaporation apparatus having a surface area of heat transfer of 3 $m^2$.

Methacrylic acid and ethylene oxide were reacted in the presence of iron powder catalyst and the resultant 2-hydroxyethyl methacrylate (including diester and other impurities) was introduced into a middle plate of the distillation column 1 with a flow rate of 1.0 t/hr. The distillation column 1 was operated in the condition of an operating pressure of 4 hPa and a reflux ratio of 0.5 and a distillate was obtained with a flow rate of 0.95 h/hr from a column top.

A bottom from the distillation column 1 was introduced into the thin-film evaporation apparatus 2. The thin-film evaporation apparatus 2 was operated with an operating pressure of 4 hPa and the distillate was returned to the distillation column 1 through a distillate line 4 comprising a condenser 3 on the way and the distillate of 0.05 t/hr was made to wasted fluid.

A constituent ratio of 2-hydroxyethyl methacrylate, diester and other impurities contained in the above supplied solution and distillate was listed in Table 1.

The above procedure was continued for three months. However, a problem of forming a polymer did not occur and the above process operated stably.

TABLE 1

| | Constitutional ratio (weight %) | | |
|---|---|---|---|
| | 2-Hydroxyethyl methacrylate | Diester | Other impurities |
| Supplied solution | 95.7 | 0.07 | 4.23 |
| Distillate | 98.5 | 0.09 | 1.41 |

COMPARATIVE EXAMPLE 1

Figure 2:
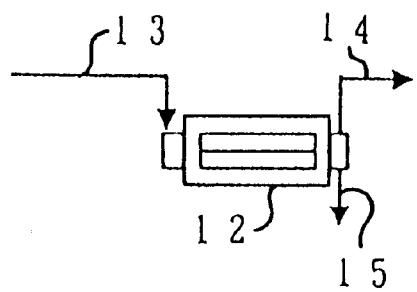
FIG. 2 is a flow chart describing the example of the purification process according to Comparative Example 1.

2-Hydroxyethyl methacrylate was purified by using a thin-film evaporation apparatus alone according to the process as described in FIG. 2. The thin-film evaporation apparatus 12 as used was a horizontal thin-film evaporation apparatus having a surface area of heat transfer of 3 m².

Methacrylic acid and ethylene oxide were reacted in the presence of iron powder catalyst and the resultant 2-hydroxyethyl methacrylate (including diester and other impurities) was introduced into the thin-film evaporation apparatus 12 with a flow rate of 0.2 t/hr. The thin-film evaporation apparatus 12 was operated in the condition of an operating pressure of 4 hPa and a distillate was obtained with a flow rate of 0.17 h/hr and the rest thereof was abandoned as waste fluid.

A constituent ratio of 2-hydroxyethyl methacrylate, diester and other impurities contained in the above supplied solution and distillate was listed in Table 2.

The above procedure was continued for three months. A problem of forming a polymer did not occur and the above process operated stably. However, the quality of the distillate is not enough.

TABLE 2

| | Constitutional ratio (weight %) | | |
|---|---|---|---|
| | 2-Hydroxyethyl methacrylate | Diester | Other impurities |
| Supplied solution | 95.7 | 0.07 | 4.23 |
| Distillate | 95.9 | 0.12 | 3.98 |

COMPARATIVE EXAMPLE 2

Figure 3:
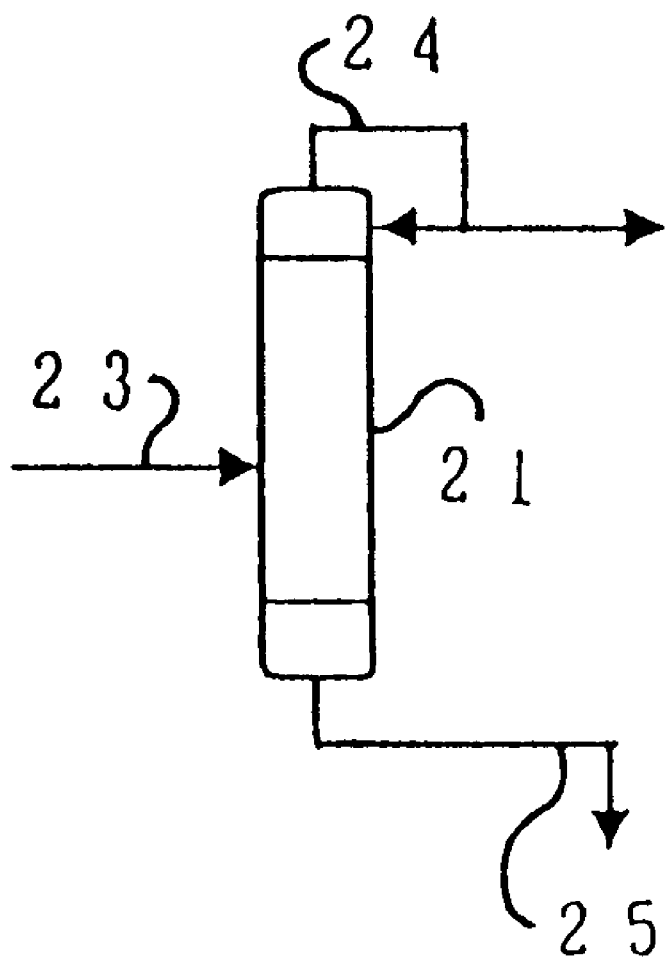
FIG. 3 is a flow chart describing the example of the purification process according to Comparative Example 2.

2-Hydroxyethyl methacrylate was purified by using a distillation column alone according to the process as described in FIG. 3. The distillation column 21 as used was a dam-free perforated-plate distillation column having five plates.

Methacrylic acid and ethylene oxide were reacted in the presence of iron powder catalyst and the resultant 2-hydroxyethyl methacrylate (including diester and other impurities) was introduced into a middle plate of the distillation column 21 with a flow rate of 1.0 t/hr. The distillation column 21 was operated in the condition of an operating pressure of 4 hPa and a reflux ratio of 0.5 and a distillate was obtained with a flow rate of 0.95 h/hr from a column top.

A bottom from the distillation column 21 was extracted with a flow rate of 0.05 t/hr and was made to wasted fluid.

A constituent ratio of 2-hydroxyethyl methacrylate, diester and other impurities contained in the above supplied solution and distillate was listed in Table 3.

The above procedure was continued. However, a problem of forming a polymer occurred after one month and the above process could not operate stably.

TABLE 3

| | Constitutional ratio (weight %) | | |
|---|---|---|---|
| | 2-Hydroxyethyl methacrylate | Diester | Other impurities |
| Supplied solution | 95.7 | 0.07 | 4.23 |
| Distillate | 98.1 | 0.48 | 1.42 |

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A purification process for hydroxyalkyl (meth)acrylate, which comprises the steps of: obtaining a reaction solution by reacting (meth)acrylic acid and alkylene oxide in the presence of a catalyst, removing unreacted alkylene oxide and/or (meth)acrylic acid in the reaction solution, and thus obtaining the hydroxyalkyl (meth)acrylate, with the purification process being characterized in that a distillation apparatus having a portion of a vacant column and a thin-film evaporation apparatus are used at the same time.

2. A purification process for hydroxyalkyl (meth)acrylate according to claim 1, wherein a bottom of the distillation apparatus is supplied to the thin-film evaporation apparatus and a distillate from the thin-film evaporation apparatus is returned to the distillation apparatus through a distillate line comprising a condenser on the way.

3. A purification process for hydroxyalkyl (meth)acrylate according to claim 1, wherein the distillation apparatus comprises a reboiler.

4. A purification process for hydroxyalkyl (meth)acrylate according to claim 1, wherein the distillation apparatus is operated at an operating pressure of 0.66 to 40 hPa and the thin-film evaporation apparatus is operated at an operating pressure of 0.66 to 40 hPa.

5. A purification process for hydroxyalkyl (meth)acrylate according to claim 1, wherein the distillation apparatus is a distillation column comprising plural sieve trays or a distillation column comprising packed materials.

* * * * *